United States Patent [19]
Boime et al.

[11] Patent Number: 5,883,073
[45] Date of Patent: Mar. 16, 1999

[54] SINGLE-CHAIN DOUBLE-ALPHA PEPTIDE

[75] Inventors: Irving Boime; David Ben-Menahem, both of St. Louis, Mo.

[73] Assignee: Washington University, St. Louis, Mo.

[21] Appl. No.: 834,802

[22] Filed: Apr. 3, 1997

[51] Int. Cl.$^6$ .................................................. A61K 38/24
[52] U.S. Cl. .............................. 514/8; 530/395; 530/397; 530/398; 530/399; 530/350; 930/110; 930/130; 930/310; 435/69.4; 435/69.7; 435/69.1; 435/325
[58] Field of Search .................................. 435/69.7, 69.1, 435/69.4, 325; 530/350, 397, 398, 395; 930/110, 130, 310; 514/8

[56] References Cited

U.S. PATENT DOCUMENTS

| | | | |
|---|---|---|---|
| 5,177,193 | 1/1993 | Boime et al. | 530/397 |
| 5,705,478 | 1/1998 | Boime | 514/8 |
| 5,712,122 | 1/1998 | Boime et al. | 435/69.7 |

FOREIGN PATENT DOCUMENTS

| | | |
|---|---|---|
| WO 90/09800 | 9/1990 | WIPO . |
| WO 91/16922 | 11/1991 | WIPO . |
| WO 96/05224 | 2/1996 | WIPO . |

OTHER PUBLICATIONS

Furuhashi et al., Molecular Endicrinology 9(1):54–63, Jan. 9, 1995.

Sugahara et al., Molecular and Cellular Endocrinology 125(1–2):71–77, Dec. 20, 1996.

LaPolt, P.S., et al., "Enhanced Stimulation of Follicle Maturation and Ovulatory Potential by Long Acting Follicle–Stimulating Hormone Agonists with Extended Carboxyl–Terminal Peptides," *Endocrinology* (1992) 131(6):2514–2510.

Fares, F.A., et al., "Design of a long–acting follitropin agonist by fusing the C–terminal sequence of the chorionic gonadotropin β subunit to the follitropin β subunit," *Proc Natl Acad Sci USA* (1992) 89:4304–4308.

Lapthorn, A.J., et al., "Crystal structure of human chorionic gonadotropin," *Nature* (1994) 369:455–461.

Wu, H., et al., "Structure of human chorionic gonadotropin at 2.6Å resolution from MAD analysis of the selenomethionyl protein," *Structure* (1994) 2(6):545–558.

Patel, D.J., "A clasped embrace," *Nature* (1994) 369:438–439.

Matzuk, M.M., et al., "The Biological Role of the Carboxyl–Terminal Extension of Human Chorionic Gonadotroin [sic] β–Subunit," *Endocrinology* (1990) 126(1):376–383.

Chen, F., et al., "The Carboxy–Terminal Region of the Glycoprotein Hormone α–Subunit: Contributions to Receptor Binding and Signaling in Human Chorionic Gonadotropin," *Molecular Endocrinology* (1992) 6(6):914–919.

Yoo, J., et al., "Cooh–terminal Amino Acids of the α Subunit Play Common and Different Roles in Human Choriogonadotropin and Follitropin," *Journal of Biological Chemistry* (1993) 268(18):13034–13042.

Yoo, J., et al., "Conversion of Lysine 91 to Methionine or Glutamic Acid in Human Choriogonadotropin α Results in the Loss of cAMP Inducibility," *Journal of Biological Chemistry* (1991) 266(27):17741–17743.

Erickson, L.D., et al., "Synthetic α–Subunit Peptides Stimulate Testosterone Production in Vitro by Rat Leydig Cells," *Enocrinology* (1990) 126(5):2555–2560.

Dayhoff, R.V., et al., "A Model of Evolutionary Change in Proteins," *Atlas of Protein Sequence and Structure* (1972) pp. 89–99.

Matzuk, M.M., et al., "Site Specificity of the Chorionic Gonadotropin N–Linked Oligosaccharides in Signal Transduction," *Journal of Biological Chemistry* (1989) 264(5):2409–2414.

Keene, J.L., et al., "Expression of Biologically Active Human Follitropin in Chinese Hamster Ovary Cells," *Journal of Biological Chemistry* (1989) 264(9):4769–4775.

Keene, J.L., et al., "Expression of Recombinant Human Choriogonadotropin in Chinese Hamster Ovary Glycosylation Mutants," *Molecular Endocrinology* (1989) 3(12):2011–2017.

Matzuk, M.M., et al., "The Glycoprotein β–Subunit is Critical for Secretion and Stability of the Human Thyrotropin α–Subunit," *Molecular Endocrinology* (1988) 2(2):95–100.

Bielinska, M., et al., "Site–Directed Mutagenesis Identifies Two Receptor Binding Domains in the Human Chorionic Gonadotropin Alpha Subunit," *J Cell Biol* (1990) 111:330A (Abstract 1844).

Furuhashi, M., et al., "Fusing the Carboxy–Terminal Peptide of the Chorionic Gonadotropin (CG) β–Subunit to the Common α–Subunit: Retention of O–Linked Glycosylation and Enhanced in Vivo Bioactivity of Chimeric Human CG," *Molecular Endocrinology* (1995) 9(1):54–63.

*Primary Examiner*—Lila Feisee
*Assistant Examiner*—Eliane Lazar-Wesley
*Attorney, Agent, or Firm*—Kate H. Murashige; Morrison & Foerster

[57] ABSTRACT

The invention is directed to a glycosylated or nonglycosylated protein which is composed of the amino acid sequence of a first α subunit common to the glycoprotein hormones linked covalently, optionally through a linker moiety, to the amino acid sequence of a second α subunit of said hormones, wherein said first and second α subunits consist of the native amino acid sequences or variants of said amino acid sequences. These proteins are useful as agonists or antagonists of glycoprotein hormone activity.

25 Claims, No Drawings

SINGLE-CHAIN DOUBLE-ALPHA PEPTIDE

ACKNOWLEDGMENT OF GOVERNMENT SUPPORT

This invention was made with government support under NIH Contract No. NO1-HD-9-2922, awarded by the National Institutes of Health. The government has certain rights in this invention.

TECHNICAL FIELD

The invention relates to the field of protein engineering and the glycoprotein hormones which occur normally as heterodimers. More specifically, the invention concerns single-chain peptides with agonist or antagonist activity for chorionic gonadotropin (CG), thyroid stimulating hormone (TSH), luteinizing hormone (LH), and follicle stimulating hormone (FSH), which single chains consist essentially of two α subunits.

BACKGROUND ART

In humans, four important glycoprotein hormone heterodimers (LH, FSH, TSH and CG) have identical α subunits and differing β subunits. Three of these hormones are present in virtually all other vertebrate species as well; CG has so far been found only in primates and in horses.

PCT application WO90/09800, published 7 Sep., 1990, and incorporated herein by reference, describes a number of modified forms of these hormones. One important modification is C-terminal extension of the β subunit of FSH, LH, and TSH by the carboxy terminal peptide (CTP) of human chorionic gonadotropin β-subunit or a variant thereof. Other muteins of these hormones are also described. The CTP-extended β subunit of FSH is also described in two papers by applicants herein: LaPolt, P. S. et al.; *Endocrinology* (1992) 131:2514–2520 and Fares, F. A. et al.; *Proc Natl Acad Sci USA* (1992) 89:4304–4308.

The crystal structure of the heterodimeric form of human chorionic gonadotropin has now been published in more or less contemporaneous articles; one by Lapthorn, A. J. et al. *Nature* (1994) 369:455–461 and the other by Wu, H. et al. *Structure* (1994) 2:545–558. The results of these articles are summarized by Patel, D. J. *Nature* (1994) 369:438–439.

PCT application WO91/16922 published 14 Nov., 1991 describes a multiplicity of chimeric and otherwise modified forms of the heterodimeric glycoprotein hormones. In general, the disclosure is focused on chimeras of α subunits or β subunits involving portions of various α or β chains respectively. One construct simply listed in this application, and not otherwise described, fuses substantially all of the β chain of human chorionic gonadotropin to the α subunit preprotein, i.e., including the secretory signal sequence for this subunit.

PCT application WO96/05224 describes single-chain forms of the glycoprotein hormone wherein the α and β subunits are covalently linked through their N- or C-termini so as to form agonists or antagonists. The linkage can be either β-α or α-β. Also described are single-chain forms wherein two β subunits are covalently linked through their termini. Preferred embodiments of such single-chain forms are fusion proteins wherein the linkage is effected through peptide bonds, optionally through additional amino acid sequence forming a "linker."

It has now been found by applicants that single-chain proteins which consist essentially of two α subunits covalently linked through their N- or C-termini, optionally through a linker moiety can behave as agonists or antagonists of the glycoprotein hormones by interacting with the relevant receptors.

DISCLOSURE OF THE INVENTION

The invention provides single-chain proteins comprised of two α subunits of the glycoprotein hormones found in most vertebrate species. These single-chain peptides may either be glycosylated, partially glycosylated, or nonglycosylated α subunits that occur in the native glycoprotein hormones or are variants of them. The two α subunits may optionally be linked through a linker moiety. Particularly preferred linker moieties include the carboxy terminal peptide (CTP) unit either as a complete unit or only as a portion thereof. The resulting single-chain peptides either mimic the activity of the unmodified heterodimeric form or are antagonists of this activity.

Thus, in one aspect, the invention is directed to a glycosylated or nonglycosylated protein which comprises the amino acid sequence of the α subunit common to the glycoprotein hormones in a species linked covalently, optionally through a linker moiety, to the amino acid sequence of an additional α subunit of the same or a different species, or variants of said amino acid sequences wherein said variants are defined herein.

In other aspects, the invention is directed to recombinant materials and methods to produce the single-chain proteins of the invention, to pharmaceutical compositions containing them; to antibodies specific for them; and to methods for their use.

MODES OF CARRYING OUT THE INVENTION

Four "glycoprotein" hormones in humans provide a family which includes human chorionic gonadotropin (hCG), follicle stimulating hormone (FSH), luteinizing hormone (LH), and thyroid stimulating hormone (TSH). As used herein, "glycoprotein hormones" refers to the members of this family. All of these hormones are heterodimers comprised of α subunits which, for a given species, are identical in amino acid sequence among the group, and β subunits which differ according to the member of the family. Thus, normally these glycoprotein hormones occur as heterodimers composed of α and β subunits associated with each other but not covalently linked. Most vertebrates produce FSH, TSH and LH; chorionic gonadotropin has been found only in primates, including humans, and horses.

Thus, this hormone "quartet" is composed of heterodimers wherein the α and β subunits of each are encoded in different genes and are separately synthesized by the host. The host then assembles the separately synthesized subunits into a non-covalently linked heterodimeric complex. In this manner, the heterodimers of this hormone quartet differ from heterodimers such as insulin which is synthesized from a single gene (in this case with an intervening "pro" sequence) and where the subunits are covalently coupled using disulfide linkages. This hormone quartet is also distinct from the immunoglobulins which are assembled from different loci, but are covalently bound through disulfide linkages.

In the peptides of the present invention, two α subunits are covalently linked to obtain a single-chain peptide. This peptide, by mimicking the conformation of the heterodimers sufficiently to bind to their receptors, may behave as either an agonist or an antagonist of the activities of one or more of the glycoprotein hormones. Alternatively, the single-chain "double α" subunit can be combined with an appropriate β subunit and the resulting heterodimeric will either mimic the behavior of the native heterodimer or antagonize its activity. As demonstrated below, the single-chain "double α" can self-assemble with the β subunit of CG.

Features of the Members of the Quartet

The β subunit of hCG is substantially larger than the other β subunits in that it contains approximately 34 additional amino acids at the C-terminus referred to herein as the carboxy terminal portion (CTP) which, when glycosylated at the O-linked sites, is considered responsible for the comparatively longer serum half-life of hCG as compared to other gonadotropins (Matzuk, M. et al., *Endocrinol* (1989) 126:376). In the native hormone, this CTP extension contains four mucin-like O-linked oligosaccharides.

In one embodiment of the present invention, the two α subunits are coupled into a single-chain proteinaceous material where the two α subunits are covalently linked through a linker moiety. The linker moiety may include further amino acid sequence, and in particular the CTP units described herein can be advantageously included in the linker. In addition, the linker may include peptide or non-peptide drugs which can be targeted to the receptors for the hormones.

In addition to the head-to-tail configuration that is achievable by simply coupling the two α chains through a peptide bond, subunits can be linked head-to-head or tail-to-tail. Head to head and tail to tail couplings involve synthetic chemistry using standard techniques to link two carboxyl or two amino groups through a linker moiety. For example, two amino groups may be linked through an anhydride or through any dicarboxylic acid derivative; two carboxyl groups can be linked through diamines or diols using standard activation techniques. However, the most preferred form is a head to tail configuration wherein standard peptide linkages suffice and the single-chain compound can be prepared as a fusion protein recombinantly or using synthetic peptide techniques either in a single chain or, preferably, ligating individual portions of the entire sequence. Of course, if desired, peptide or non-peptide linker moieties can be used in this case as well, but this is unnecessary and the convenience of recombinant production of the single-chain protein would suggest that embodiments that permit this method of production comprise by far the most preferred approach.

The "double α" single-chain compounds of the invention may be designed to contain tandem copies of the same α subunit, or α subunits derived from different species may be used or identical or different variants may be employed. Chimeric forms of α subunits can also be used in the single-chain compounds which couple two α subunits into a single molecule. When a head-to-tail configuration is employed, linkers may be absent or may consist essentially of additional peptide sequence, preferably a complete or partial CTP.

The "double α" single-chain peptides are especially useful as antagonists or agonists for the receptors normally activated by the heterodimeric glycoprotein hormones. Since the α subunit is believed largely responsible for signal transduction, and since the α and β subunits have similar conformations, the single-chain compounds should be able specifically to bind a receptor and, depending on the nature of the linkage and the variants that may represent the α subunits, activate or block the receptor. In addition, the double α single-chain peptide may be associated with β subunits and the resulting heterodimers may be used in analogous ways.

The receptor-binding activity of the "double α" single-chain tandem peptides is based in part on the crystal structure of the heterodimers. It is noted that the α and β chains have similar cystine-knot configurations and that some of the folding patterns of the two chains are analogous.

The following definitions may be helpful in describing the "double α" forms of the molecules.

As used herein, α subunit, and FSH, LH, TSH, and CG β subunits as well as the heterodimeric forms have in general their conventional definitions and refer to the proteins having the amino acid sequences known in the art per se, or allelic variants thereof, regardless of the glycosylation pattern exhibited.

"Native" forms of these peptides are those which have the amino acid sequences isolated from the relevant vertebrate tissue, and have these known sequences per se, or their allelic variants.

"Variant" forms of these proteins are those which have deliberate alterations in amino acid sequence of the native protein produced by, for example, site-specific mutagenesis or by other recombinant manipulations, or which are prepared synthetically.

These alterations consist of 1–10, preferably 1–8, and more preferably 1–5 amino acid changes, including deletions, insertions, and substitutions, most preferably conservative amino acid substitutions as defined below. The resulting variants must retain activity which affects the corresponding activity of the native hormone—i.e., either they must retain the biological activity of the native hormone directly, or they must behave as antagonists, generally by virtue of being able to bind the receptors for the native hormones but lacking the ability to effect signal transduction. For example, it is known that if the glycosylation site at position 52 of the α subunit is removed by an amino acid substitution, therefore preventing all glycosylation at that site, the hormones which are heterodimers with this altered α subunit are generally antagonists and are able to bind receptors preventing the native hormone from doing so in competition. (On the other hand, the glycosylation site of the α subunit at position 78 appears not greatly to affect the activity of the hormones.) Other alterations in the amino acid sequence may also result in antagonist rather than agonist activity for the variant.

One set of preferred variants are those wherein the glycosylation sites of either the α or β subunits or both have been altered. The α subunit contains two glycosylation sites, one at position 52 and the other at position 78, and the effect of alterations of these sites on activity has just been described. Similarly, the β subunits generally contain two N-linked glycosylation sites (at positions that vary somewhat with the nature of the β chain) and similar alterations can be made at these sites. The CTP extension of hCG contains four O-linked glycosylation sites, and conservative mutations at the serine residues (e.g., conversion of the serine to alanine) destroys these sites. Destruction of the O-linked glycosylation sites may effect conversion of agonist activity to antagonist activity.

Finally, alterations in amino acid sequence that are proximal to the N-linked or O-linked glycosylation sites influence the nature of the glycosylation that is present on the resulting molecule and also alter activity.

Alterations in amino acid sequence also include both insertions and deletions. Thus, truncated forms of the hormones are included among variants, e.g., mutants of the α subunit which are lacking some or all of the amino acids at positions 85–92 at the C-terminus. In addition, α subunits with 1–10 amino acids deleted from the N-terminus are included. Some useful variants of the hormone quartet described herein are set forth in U.S. Pat. No. 5,177,193 issued 5 Jan., 1993 and incorporated herein by reference. As shown therein, the glycosylation patterns can be altered by destroying the relevant sites or, in the alternative, by choice of host cell in which the protein is produced.

As explained above, the single chain forms are convenient starting materials for various engineered muteins. Such muteins include those with non-critical regions altered or removed. Such deletions and alterations may comprise entire loops, so that sequences of considerably more than 10 amino acids may be deleted or changed. The single chain molecules must, however, retain at least the receptor binding domains and/or the regions involved in signal transduction.

There is considerable literature on variants of the hormone quartet described herein and it is clear from this literature that a large number of possible variants which result both in agonist and antagonist activity can be prepared. Such variants are disclosed, for example, in Chen, F. et al. *Molec Endocrinol* (1992) 6:914–919; Yoo, J. et al *J Biol Chem* (1993) 268:13034–13042; Yoo, J. et al. *J Biol Chem* (1991) 266:17741–17743; Puett, D. et al. *Glycoprotein Hormones,* Lusbader, J. W. et al. EDS, Springer Verlag, New York (1994) 122–134; Kuetmann, H. T. et al. (ibid) pages 103–117; Erickson, L. D. et al. *Endocrinology* (1990) 126:2555–2560; and Bielinska, M. et al. *J Cell Biol* (1990) 111:330a (Abstract 1844).

In the single-chain forms of the present invention, either or both α subunits may contain a CTP extension inserted into a noncritical region. "Noncritical" regions are those regions not required for biological activity (including agonist and antagonist activity). In general, these regions are removed from binding sites, precursor cleavage sites, and catalytic regions. Regions critical for inducing proper folding, binding to receptors, catalytic activity and the like should be avoided; similarly, regions which are critical to assure the three-dimensional conformation of the protein should be avoided. It should be noted that some of the regions which are critical in the case of the dimer become non-critical in the single chain forms since the conformational restriction imposed by the single chain may obviate the necessity for these regions. The ascertainment of non-critical regions is readily accomplished by deleting or modifying candidate regions and conducting an appropriate assay for the desired activity. Regions where modifications result in loss of activity are critical; regions wherein the alteration results in the same or similar activity (including antagonist activity) are considered noncritical.

It should be emphasized, that by "biological activity" is meant activity which is either agonistic or antagonistic to that of the native hormones. Thus, certain regions are critical for behavior of a variant as an antagonist, even though the antagonist is unable to directly provide the physiological effect of the hormone.

For example, for the a subunit, positions 33–59 are thought to be necessary for signal transduction and the 20 amino acid stretch at the carboxy terminus is needed for signal transduction/receptor binding. Where the noncritical region is "proximal" to the N- or C-terminus, the insertion is at any location within 10 amino acids of the terminus, preferably within 5 amino acids, and most preferably at the terminus per se.

In general, "proximal" is used to indicate a position which is within 10 amino acids, preferably within five amino acids, of a referent position, and most preferably at the referent position per se. Thus, certain variants may contain substitutions of amino acids "proximal" to a glycosylation site; the definition is relevant here. In addition, the α subunits may be linked to each other at positions "proximal" to their N- or C-termini.

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP.

By a "partial" CTP unit is meant an amino acid sequence which occurs between positions 112–118 to 145 inclusive, but which has at least one amino acid deleted from the shortest possible "complete" CTP unit (i.e. from positions 118–145). The "partial" CTP units included in the invention preferably contain at least one O-glycosylation site if agonist activity is desired. Some nonglycosylated forms of the hormones are antagonists and are useful as such. The CTP unit contains four such sites at the serine residues at positions 121 (site 1); 127 (site 2); 132 (site 3); and 138 (site 4). The partial forms of CTP useful in agonists of the invention will contain one or more of these sites arranged in the order in which they appear in the native CTP sequence. Thus, the "partial" CTP unit employed in agonists of the invention may include all four glycosylation sites; sites 1, 2 and 3; sites 1, 2 and 4; sites 1, 3 and 4; sites 2, 3 and 4; or simply sites 1 and 2; 1 and 3; 1 and 4; 2 and 3; 2 and 4; or 3 and 4; or may contain only one of sites 1, 2, 3 or 4.

Variants

The α subunits (and any β subunits with which they may associate) and the CTP units may correspond exactly to the native hormone or CTP sequence, or may be variants. In such variants, 1–10, preferably 1–8, and most preferably 1–5 of the amino acids contained in the native sequence are substituted by a different amino acid compared to the native amino acid at that position, or 1–10, more preferably 1–8 and most preferably 1–5 amino acids are simply deleted or combination of these. As pointed out above, when non-critical regions of the single chain forms are identified, in particular, through detecting the presence of non-critical "loops", the number of amino acids altered by deletion or substitution may be increased to 20 or 30 or any arbitrary number depending on the length of amino acid sequence in the relevant non-critical region. Of course, deletion or substitutions in more than one non-critical region results in still greater numbers of amino acids in the single chain forms being affected and substitution and deletions strategies may be used in combination. The substitutions or deletions taken cumulatively do not result in substantial elimination of agonist or antagonist activity associated with the hormone. Substitutions by conservative analogs of the native amino acid are preferred.

"Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. In general, acidic amino acids fall into one group; basic amino acids into another; neutral hydrophilic amino acids into another; and so forth.

If the single-chain proteins of the invention are constructed by recombinant methods, they will contain only gene encoded amino acid substitutions; however, if any portion is synthesized by standard, for example, solid phase, peptide synthesis methods and ligated, for example, enzymatically, into the remaining protein, non-gene encoded amino acids, such as aminoisobutyric acid (Aib), phenylglycine (Phg), and the like can also be substituted for their analogous counterparts.

These non-encoded amino acids also include, for example, β-alanine (β-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); J-2-thienylalanine (Thi); and methionine sulfoxide (MSO). These also fall conveniently into categories of conservative properties.

Thus, amino acid substitutions other than those encoded in the gene can also be included in peptide compounds within the scope of the invention and conservative substitutions are evaluated with respect to the same criteria as with respect to the gene-encoded amino acids.

Preferred Embodiments of the Single-Chain Hormones

The single-chain hormones of the invention are most efficiently and economically produced using recombinant techniques. Therefore, those forms of α subunits, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids are also within the scope of the invention.

In the most preferred embodiments of the single-chain hormones of the invention, the C-terminus of one α subunit is covalently linked, optionally through a linker, to the N-terminus of the other α subunit. The linkage can be a direct peptide linkage wherein the C-terminal amino acid of one α subunit is directly linked through the peptide bond to the N-terminus of the other; however, in many instances it is preferable to include a linker moiety between the two termini. The linker moiety is preferably hydrophilic and flexible.

It should be understood that in discussing linkages between the termini of the subunits comprising the single chain forms, one or more termini may be altered by substitution and/or deletion as described above.

In one particularly preferred set of embodiments, the linker moiety will include one or more CTP units and/or variants or truncated forms thereof. Further, the linker moiety may include a drug covalently, preferably releasably, bound to the linker moiety. Means for coupling the drug to the linker moiety and for providing for its release are conventional. Thus, while CTP units are preferred inclusions in the linker moiety, it is understood that the linker may be any suitable covalently bound material which provides the appropriate spatial relationship between the two α subunits. Thus, for head-to-tail configurations the linker may generally be a peptide comprising an arbitrary number, but typically less than 100, more preferably less than 50 amino acids which has the proper hydrophilicity/hydrophobicity ratio to provide the appropriate spacing and confirmation in solution. In general, the linker should be on balance hydrophilic so as to reside in the surrounding solution and out of the way of the interaction between the two α subunits. It is preferable that the linker include β turns typically provided by proline residues. Any suitable polymer, including peptide linkers, with the above-described correct characteristics may be used.

Preferred Embodiments of CTP Units

The notation used for the CTP units of the invention is as follows: for portions of the complete CTP unit, the positions included in the portion are designated by their number as they appear in FIG. 2 herein. Where substitutions occur, the substituted amino acid is provided along with a superscript indicating its position. Thus, for example, CTP (120–143) represents that portion of CTP extending from positions 120 to 143; CTP (120–130; 136–143) represents a fused amino acid sequence lacking positions 118–119, 131–135, and 144–145 of the native sequence. CTP ($Arg^{122}$) refers to a variant wherein the lysine at position 122 is substituted by an arginine; CTP ($Ile^{134}$) refers to a variant wherein the leucine at position 134 is substituted by isoleucine. CTP ($Val^{128}Val^{143}$) represents a variant wherein two substitutions have been made, one for the leucine at position 128 and the other for the isoleucine at position 142. CTP (120–143; $Ile^{128} Ala^{130}$) represents the relevant portion of the CTP unit where the two indicated substitutions have been made.

Also preferred among variants of CTP are those wherein one or more of the O-linked glycosylation sites have been altered or deleted. One particularly preferred means of altering the site to prevent glycosylation is substitution of an alanine residue for the serine residue in these sites.

Particularly preferred are those CTP units of the following formulas:

1 CTP (116–132)
2 CTP (118–128; 130–135)
3 CTP (117–142)
4 CTP (116–130)
5 CTP (116–123; 137–145)
6 CTP (115–133; 141–145)
7 CTP (117–140, $Ser^{123}Gln^{140}$)
8 CTP (125–143, $Ala^{130}$)
9 CTP (135–145, $Glu^{139}$)
10 CTP (131–143, $Val^{142}Val^{143}$)
11 CTP (118–132)
12 CTP (118–127)
13 CTP (118–145)
14 CTP (115–132)
15 CTP (115–127)
16 CTP (115–145)
17 CTP (112–145)
18 CTP (112–132)
19 CTP (112–127)

Preferred Embodiments of the α Subunits

Of course, the native forms of the α subunits in the single-chain form are among the preferred embodiments. However, certain variants are also preferred.

In particular, variants of the α subunit in which the N-linked glycosylation site at position 52 is eliminated or altered by amino acid substitutions at or proximal to this site are preferred for antagonist activity. Similar modifications at the glycosylation site at position 78 are also preferred. Deletion or alteration of one or more amino acids at positions 85–92 also affects the nature of the activity of hormones containing the α subunit and substitution or deletion of amino acids at these positions is also among the preferred embodiments.

When the "double α" is coupled with a β subunit, variants of the β subunit are also included. The N-linked glycosylation sites in the β chain can conveniently be modified to eliminate glycosylation and thus affect the agonist or antagonist activity of the β chains. If CTP is present, either natively as in CG or by virtue of being present as a linker, the O-linked glycosylation sites in this moiety may also be altered.

Particular variants containing modified or deleted glycosylation sites are set forth in Yoo, J. et al. *J Biol Chem* (1993) 268:13034–13042; Yoo, J. et al. *J Biol Chem* (1991) 266:17741–17743; and Bielinska, M. et al. *J Cell Biol* (1990) 111:330a (all cited above) and in Matzuk, M. M. et al. *J Biol Chem* (1989) 264:2409–2414; Keene, J. L. et al. *J Biol Chem* (1989) 264:4769–4775; and Keene, J. L. et al. *Mol Endocrinol* (1989) 3:2011–2017.

Not only may the glycosylation sites per se be modified directly, but positions proximal to these sites are preferentially modified so that the glycosylation status of the mutant will be affected. For the α subunit, for example, variants in which amino acids between positions 50–60 are substituted, including both conservative and nonconservative substitutions, are favored, especially substitutions at positions 51, 53 and 55 because of their proximity to the glycosylation site at $Asn_{52}$. Also preferred are mutants of the α subunit wherein lysine at position 91 is converted to methionine or glutamic acid.

Although the variants have been discussed in terms of variations in the individual subunits hereinabove, it will be recalled that the single chain "double α" offers additional opportunities for modification. Specifically, regions that are critical to folding of the native heterodimer may not be critical to the correct conformation of the "double α" and these regions are available for variation, although not described above in terms of individual members of the heterodimeric forms. Further, the "double α" may be modified dramatically in the context of non-critical regions whose alteration and/or deletion do not affect the biological activity as described above.

Suitable Drugs

Suitable drugs that may be included in the linker moiety include peptides or proteins such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Peptide- or protein-based drugs have the advantage that they can be included in the single-chain and the entire construct can readily be produced by recombinant expression of a single gene. Also, small molecule drugs such as antibiotics, antiinflammatories, toxins, and the like can be used.

In general, the drugs included within the linker moiety will be those desired to act in the proximity of the receptors to which the hormones ordinarily bind. Suitable provision for release of the drug from inclusion within the linker will be provided, for example, by also including sites for enzyme-catalyzed lysis as further described under the section headed Preparation Methods hereinbelow.

Other Modifications

The double α proteins of the invention may be further conjugated or derivatized in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

The glycosylation status of the peptides of the invention is particularly important. They may be prepared in nonglycosylated form either by producing them in procaryotic hosts or by mutating the glycosylation sites normally present in the subunits and/or any CTP units that may be present. Both nonglycosylated versions and partially glycosylated versions of the double α and any associated β subunit can be prepared by manipulating the glycosylation sites. Normally, glycosylated versions are, of course, also included within the scope of the invention.

As is generally known in the art, the double α of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels is particularly helpful for these proteins since they are targeting agents receptor ligand.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the proteins of the invention to solid supports. When coupled, these proteins can then be used as affinity reagents for the separation of desired components with which specific reaction is exhibited.

Preparation Methods

Methods to construct the proteins of the invention are well known in the art. As set forth above, if only gene encoded amino acids are included, and the single-chain is in a head-to-tail configuration, the most practical approach at present is to synthesize these materials recombinantly by expression of the DNA encoding the desired protein. DNA containing the nucleotide sequence encoding the single-chain forms, including variants, can be prepared from native sequences. Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including procaryotic hosts such as bacteria and eucaryotic hosts such as yeast, plant cells, insect cells, mammalian cells, avian cells, and the like.

The choice of host is particularly to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the α subunit, whether the α subunit is modified or unmodified, is the "minigene" construction.

As used herein, the α subunit "minigene" refers to the gene construction disclosed in Matzuk, M. M., et al, *Mol Endocrinol* (1988) 2:95–100, in the description of the construction of pM$^2$/CG α or pM$^2$/α. This "minigene" is characterized by retention only of the intron sequence between exon 3 and exon 4, all upstream introns having been deleted. In the particular construction described, the N-terminal coding sequences which are derived from exon 2 and a portion of exon 3 are supplied from cDNA and are ligated directly through an XbaI restriction site into the coding sequence of exon 3 so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the α subunit which retain the intron between exons III and IV, or any other intron and preferably no other introns.

For recombinant production, modified host cells using expression systems are used and cultured to produce the desired protein. These terms are used herein as follows:

A "modified" recombinant host cell, i.e., a cell "modified to contain" with the recombinant expression systems of the invention, refers to a host cell which has been altered to contain this expression system by any convenient manner of introducing it, including transfection, viral infection, and so forth. "Modified" refers to cells containing this expression system whether the system is integrated into the chromosome or is extrachromosomal. The "modified" cells may either be stable with respect to inclusion of the expression system or not. In short, "modified" recombinant host cells with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, additional nucleotide sequences encoding a signal peptide are also included so as to produce the signal peptide operably linked to the desired single-chain hormone to produce the preprotein. Upon secretion, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art. Synthesized portions may be ligated, and release sites for any drug contained in the linker moiety introduced by standard chemical means. For those embodiments which contain amino acids which are not encoded by the gene and those embodiments wherein the head-to-head or tail-to-tail configuration is employed, of course, the synthesis must be at least partly at the protein level. Head-to-head junctions at the natural N-termini or at positions proximal to the natural N-termini may be effected through linkers which contain functional groups reactive with amino groups, such as dicarboxylic acid derivatives. Tail-to-tail configurations at the C-termini or positions proximal to the C-termini may be effected through linkers which are diamines, diols, or combinations thereof.

Antibodies

The proteins of the invention may be used to generate antibodies specifically immunoreactive with these new compounds, not with their previously existent component parts. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention.

By "immunospecific for the double α" is meant antibodies which are immunoreactive with the double α, but not with the glycoprotein heterodimers per se or with the α subunit or linker per se within the general parameters considered to determine affinity or nonaffinity. It is understood that specificity is a relative term, and an arbitrary limit could be chosen, such as a difference in immunoreactivity of 100-fold or greater. Thus, an immunospecific antibody included within the invention is at least 100 times more reactive with the single-chain protein than with the corresponding heterodimer or α subunit.

Formulation

The proteins of the invention are formulated and administered using methods comparable to those known for the heterodimers corresponding to the single-chain form. Thus, formulation and dosage administration methods will vary according to the intended use.

Formulations for proteins of the invention are those typical of protein or peptide drugs such as found in *Remington's Pharmaceutical Sciences,* latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches.

Oral administration is also possible provided the formulation protects the peptides of the invention from degradation in the digestive system.

Optimization of dosage regimen and formulation is conducted as a routine matter and as generally performed in the art.

Methods of Use

The "double α" peptides of the invention may be used in diagnosis, therapy, and analysis. The agonist forms of the single-chain hormones of the invention can be used in treatment of infertility, as aids in in vitro fertilization techniques, and other therapeutic methods associated with the native hormones.

The single-chain hormones are also useful as reagents in a manner similar to the heterodimers.

In addition, the single-chain hormones of the invention may be used as diagnostic tools to detect the presence or absence of antibodies with respect to the native proteins in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The single-chain hormones of the invention are also useful in detecting and purifying receptors to which the native hormones bind. Thus, the single-chain hormones of the invention may be coupled to solid supports and used in affinity chromatographic preparation of receptors or antihormone antibodies. The resulting receptors are themselves useful in assessing hormone activity for candidate drugs in screening tests for therapeutic and reagent candidates.

Finally, the antibodies uniquely reactive with the single-chain hormones of the invention can be used as purification tools for isolation of subsequent preparations of these materials. They can also be used to monitor levels of the single-chain hormones administered as drugs.

The following examples are intended to illustrate but not to limit the invention.

EXAMPLE 1

Preparation of DNA Encoding α-CTP-α

This example shows the construction of an expression vector for the single-chain double α wherein the C-terminus of the α human subunit is linked through a CTP derived from positions 118–145 of human βCG to the N-terminus of an additional human α subunit.

Two plasmids were used. One, designated pM² α-C, contains the complete coding sequence for the α subunit (including the signal peptide) and the CTP sequence 188–145 of the CGβ subunit (*Mol Endocrinol* (1995) 9:54–63. The other, pM2 FCα, contains the coding sequence for a single-chain FSH wherein the FSHβ subunit is linked to the α subunit through the CTP residues 118–145 (*J Biol Chem* (1996) 271:10445). pM² α-C was digested with Apa I which cleaves at a site encoding Pro at position 137 of the CTP. pM2 FCα was digested with Apa I to generate a 1 Kb fragment containing residues 138–145 of CBβ CTP and the α subunit without signal peptide (i.e., residues 1–92). This fragment was ligated into the Apa-digested pM² α-C. This final construct expresses $HN_2$-α (with signal peptide)—CTP (28 amino acids)-α (without signal peptide)—COOH when transfected into CHO cells.

EXAMPLE 2

Production and Activity of α-CTP-α

The expression vector constructed in Example 1 was transfected into Chinese hamster ovary (CHO) cells fed $^{35}$S-cysteine (55 μCi/ml) and production of the protein was assessed by running radiolabeled protein on SDS gels. The results showed that the α-CTP-α subunit was secreted into the medium efficiently.

In addition, the "double α" gene was cotransfected into CHO cells with the βCG gene. The association of the two secreted subunits was assessed using SDS PAGE and receptor binding. The results show that double α was able to associate as a heterodimer with the βCG subunit. The heterodimer was demonstrated to be a CG agonist.

We claim:

1. A single chain glycosylated or unglycosylated protein of the formula:

wherein each α is independently the common glycoprotein hormone α subunit of FSH, TSH, LH or CG of a vertebrate species, n is 0 or 1, and "linker" is a linker moiety; and wherein:
 the amino acid sequence of said first α-subunit is linked through the C-terminal carboxyl group or N-terminal amino group thereof, optionally through said linker moiety, to the C-terminal carboxyl or to the N-terminal amino group of the amino acid sequence of said second α-subunit,
 wherein said α-subunits consist of the native amino acid sequences of said α-subunits or chimeric forms thereof or variants thereof,
 wherein said variants contain alterations of 1–10 amino acids in a native α-subunit, said alterations including deletions, insertions and substitutions or wherein said variant comprises deletion or changes in a single non-critical loop; and
 wherein said single-chain protein is an antagonist with respect to a glycoprotein hormone receptor or wherein said protein, when associated with a β-subunit of said FSH, TSH, LH or CG is an agonist of said glycoprotein receptor.

2. The protein of claim 1 wherein said protein includes said linker moiety.

3. The protein of claim 2 wherein said linker moiety includes a drug to be targeted to the receptor for the glycoprotein hormone.

4. The protein of claim 1 wherein the α subunits are human α subunits or their variants.

5. The protein of claim 1 wherein the first or second α subunits or both are modified by the insertion of a complete or partial carboxy terminal peptide (CTP) unit or variant thereof into a noncritical region thereof and/or wherein said linker moiety includes a complete or partial CTP unit or variant thereof
 wherein said partial CTP unit contains at least one glycosylation site and a variant contains 1–10 amino acid alterations.

6. The protein of claim 5 wherein said partial CTP unit consists of positions 112–132; 115–132; 116–132; or 118–132; or 112–127; 115–127; 116–127; or 118–127.

7. The protein of claim 5 wherein said CTP has one or more O-linked glycosylation sites modified or deleted.

8. The protein of claim 7 wherein said modification consists of substituting an alanine for the serine of said site.

9. The protein of claim 1 wherein one or both of the N-linked glycosylation sites of the α subunit have been modified.

10. The protein of claim 1 which is nonglycosylated.

11. The protein of claim 1 wherein one or more amino acids at positions 85–92 of the first of second α subunits or both have been deleted.

12. The protein of claim 1 wherein said variants contain 1–5 conservative amino acid substitutions as referred to the native forms or are truncated forms of said sequences or both.

13. The protein of claim 1 associated with a β-subunit of the glycoprotein hormone TSH, FSH, LH or CG to form a heterodimer.

14. The protein of claim 13 wherein the β subunit contains a modification in one or more N-linked glycosylation sites.

15. A pharmaceutical composition which comprises the protein of claim 1 in admixture with a suitable pharmaceutical excipient.

16. The protein of claim 1 coupled to a solid support.

17. A DNA or RNA molecule which comprises a nucleotide sequence encoding the protein of claim 1.

18. An expression system for the production of a single-chain protein of the formula α-(linker)$_n$-α wherein each α is independently the common glycoprotein hormone a subunit of FSH, TSH, LH or CG of a vertebrate species, n is 0 or 1, and "linker" is an amino acid sequence; and wherein the amino acid sequence of said first α-subunit is linked through the C-terminal carboxyl group thereof, optionally through said linker moiety, to the N-terminal group of the amino acid sequence of said second α-subunit, which expression system comprises a first nucleotide sequence encoding the protein of claim 1 operably linked to control sequences capable of effecting the expression of said first nucleotide sequence.

19. The expression system of claim 18 which further contains a second nucleotide sequence encoding a signal peptide operably linked to the protein encoded by said first nucleotide sequence.

20. A host cell modified to contain the expression system of claim 18.

21. A method to produce a single-chain protein protein of the formula α-(linker)$_n$-α wherein each α is independently the common glycoprotein hormone α subunit of FSH, TSH, LH or CG of a vertebrate species, n is 0 or 1, and "linker" is an amino acid sequence; and wherein the amino acid sequence of said first α-subunit is linked through the C-terminal carboxyl group thereof, optionally through said linker moiety, to the N-terminal group of the amino acid sequence of said second α-subunit, which method comprises culturing the cells of claim 20 under conditions wherein said protein is produced; and recovering said protein from the culture.

22. The method of claim 21 wherein said cells are prokaryotic cells.

23. The method of claim 21 wherein said cells are mammalian cells.

24. The method of claim 21 wherein said cells are yeast cells.

25. The method of claim 21 wherein said cells are insect cells.

* * * * *